(12) United States Patent
Dehaudt et al.

(10) Patent No.: US 11,667,410 B2
(45) Date of Patent: Jun. 6, 2023

(54) DEVICE FOR PREPARING A COSMETIC COMPOSITION AND ASSOCIATED PREPARATION PROCESS

(71) Applicant: L'OREAL, Paris (FR)

(72) Inventors: Eric Dehaudt, Clichy (FR); Thomas Pocard, Chevilly la Rue (FR)

(73) Assignee: L'OREAL, Paris (FR)

( * ) Notice: Subject to any disclaimer, the term of this patent is extended or adjusted under 35 U.S.C. 154(b) by 127 days.

(21) Appl. No.: 17/295,937

(22) PCT Filed: Nov. 21, 2019

(86) PCT No.: PCT/EP2019/082130
§ 371 (c)(1),
(2) Date: May 21, 2021

(87) PCT Pub. No.: WO2020/104609
PCT Pub. Date: May 28, 2020

(65) Prior Publication Data
US 2021/0394937 A1 Dec. 23, 2021

(30) Foreign Application Priority Data
Nov. 23, 2018 (FR) ...................................... 18 71775

(51) Int. Cl.
*B65B 3/12* (2006.01)
*A45D 33/00* (2006.01)
(Continued)

(52) U.S. Cl.
CPC ................ *B65B 3/12* (2013.01); *A45D 33/00* (2013.01); *A45D 34/00* (2013.01); *A45D 40/00* (2013.01); *A45D 2034/005* (2013.01)

(58) Field of Classification Search
CPC .... B65B 3/12; B65B 3/10; B65B 3/14; A45D 33/00; A45D 34/00; A45D 40/00; A45D 2034/005; A45D 33/24
(Continued)

(56) References Cited

U.S. PATENT DOCUMENTS 5,433,545 A * 7/1995 Keil .......................... B43K 8/10
401/199
6,729,786 B1 * 5/2004 Tufts ..................... B05C 17/002
401/133

FOREIGN PATENT DOCUMENTS

| CN | 105899101 A | 8/2016 |
| JP | H 03-206017 A | 9/1991 |
| WO | WO 2016/120333 A1 | 8/2016 |

* cited by examiner

*Primary Examiner* — David J Walczak
(74) *Attorney, Agent, or Firm* — Polsinelli PC

(57) ABSTRACT

A device (10) for preparing a cosmetic combination (12), comprising: a structure (28) extending along a longitudinal axis (X-X'), receiving at least one capsule (16) containing at least one component of a cosmetic composition (12), an outlet nozzle (32) opening at one end (34), fluidically connected to a receptacle (14) or to a preform, and a piston (36) free to move in translation along the longitudinal axis (X-X') suitable for perforating the or each capsule (16) and conveying contents of each capsule (16) to the outlet nozzle (32). The device (10) comprises at least one planar support (17) carrying in an integral manner a cosmetic product, with each planar support (17) being arranged in the housing (30), with at least one portion of each support (17) being arranged to be driven by the piston (36) to the receptacle (14) containing the cosmetic composition (12).

20 Claims, 5 Drawing Sheets

Figure 1:
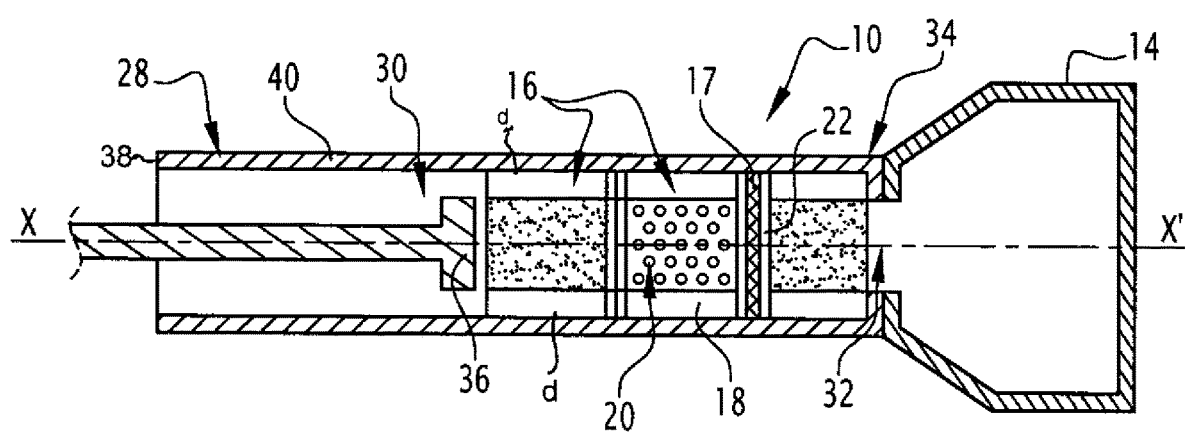

(51) Int. Cl.
*A45D 34/00* (2006.01)
*A45D 40/00* (2006.01)
(58) Field of Classification Search
USPC ..................................... 401/40–44, 132–135
See application file for complete search history.

DEVICE FOR PREPARING A COSMETIC COMPOSITION AND ASSOCIATED PREPARATION PROCESS

CROSS REFERENCE TO RELATED APPLICATIONS

This application is a National Phase filing under 35 U.S.C. § 371 of PCT/EP2019/082130 filed on Nov. 21, 2019; which application in turn claims priority to Application No. 18 71775 filed in France on Nov. 23, 2018. The entire contents of each application are hereby incorporated by reference.

The present invention relates to a device for preparing a cosmetic composition, the device comprising:

a structure defining a housing extending along a longitudinal axis, the housing receiving at least one capsule, the or at least one of the capsules containing at least one component of the cosmetic composition, an outlet nozzle opening at one end of the housing, suitable for being fluidically connected to a receptacle or to a preform intended to form a receptacle, and a piston free to move in translation in relation to the structure along the longitudinal axis in the housing, suitable for perforating the or each capsule and conveying contents of each capsule to the outlet nozzle, The invention also relates to a process for preparing such a cosmetic composition.

The cosmetic composition prepared by means of the device particularly comprises a cosmetic body surface care, coloring or makeup product, in particular a keratin surface, in particular skin, hair, nails, eyelashes, eyebrows, lips, and others.

More generally, a cosmetic composition comprises one or a plurality of cosmetic products, as defined in EC Regulation No. 1223/2009 of the European Parliament and the Council of Nov. 30, 2009, relating to cosmetic products.

The cosmetic compositions are generally commercially available prepared in advance, and packaged in customized individual containers well suited to store distribution.

This type of packaging enables a satisfactory shelf-life and easy handling of the cosmetic composition. Furthermore, it provides the consumer with a guarantee that the packaging contents match the claimed composition, and that they are in compliance with applicable standards.

However, this type of product is not ideal for all clients. Indeed, it does not allow customization of the quantity or precise contents of the cosmetic composition beyond predetermined options. Furthermore, it is not as well-suited to small-scale distribution, for example for retail outlets, that do not always use the section layouts common in stores and superstores.

Devices for filling a container with a cosmetic product extracted from a capsule are known in the prior art, for example in the document FR 3007014. However, these devices do not allow customization of the composition. Furthermore, they do not guarantee that the packaged composition has not been exposed to external contaminants or has not received an additional compound not included in the desired composition. These situations may result in risks of a reduction in product quality, or even health risks.

There is thus a need for a means of preparing and dispensing cosmetics enabling greater customization and being more suitable for retail outlets, while retaining the option of guaranteeing the type and quality of the compositions dispensed.

In addition, certain specific products are used in very small quantities, such as perfumes or colorants, which can complicate the introduction thereof in situ in the cosmetic composition. As these products have pronounced effects, an error in the quantity introduced can have substantial consequences on the quality of the composition obtained.

One aim of the invention is thus that of providing a method for dispensing cosmetics prepared in-situ in a customized manner, and allowing for the introduction of specific cosmetic products in very small quantities into the prepared cosmetic composition.

To this effect, the purpose of the invention is a device of the type mentioned above, in which the device comprises at least one planar support carrying in an integral manner a cosmetic product, with each planar support being arranged in the housing, with at least one portion of each support being arranged in order to be driven by the piston to the receptacle containing the cosmetic composition.

Such a device makes it possible to introduce compounds in small quantities into the prepared cosmetic composition, in a simple, reliable and reproducible way.

According to particular embodiments, the device according to the invention has one or several of the following characteristics, taken independently or in any technically feasible combination:

The cosmetic product is imprinted on the support, adsorbed on the support, or soaks the support.

This characteristic facilitates the handling of the support that receives the cosmetic product.

The support is made from paper, fabric, gelatin or a polymer material.

This characteristic simplifies the confection and the preparation of the support.

The support has a longitudinal extension, measured parallel to the longitudinal axis, and a transversal extent, measured perpendicularly to the longitudinal axis, with the longitudinal extent being less than the transversal extend, in particular five times less, advantageously ten times less.

This characteristic facilitates the introduction of the support into the housing for receiving capsules.

The transversal extent of the support is less than an inner diameter of the housing, measured perpendicularly to the longitudinal axis.

This characteristic facilitates the routing of the support through the housing to the receptacle of the cosmetic composition.

The support is arranged in contact with at least one of the capsules, advantageously inserted between two of the capsules.

This characteristic secures the maintaining in place of the capsules and of the support in the housing during the preparation of the cosmetic composition.

The support forms a seal that is part of one of the capsules, with the support being connected to the side walls of the capsule.

This characteristic reduces the number of objects to be introduced into the housing, which simplifies the steps of handling.

The support is formed from a cutout from a sheet that carries at least one region of cosmetic product.

The support is a tongue folded at least one time on itself in such a way as to define several successive layers perpendicular to the central axis X-X'.

These characteristics allow for a precise and rapid dosing of the quantity of product introduced through the support.

The invention further relates to a process for preparing a cosmetic composition, comprising the following steps:

provision of a device such as described above;

positioning of the or of each capsule in the housing;

positioning of the or of each support in the housing;

positioning of a receptacle or a preform intended to form a receptacle, connected to the outlet nozzle;

movement of the piston in the housing along the longitudinal axis toward the end, perforation of each capsule on either side of the capsule and conveyance of the contents of each capsule as well as at least one portion of each support toward the end; and extrusion of the contents of each capsule and of at least one portion of each support into the receptacle or against the preform, through the outlet nozzle, and obtaining the cosmetic composition.

Figure 2:
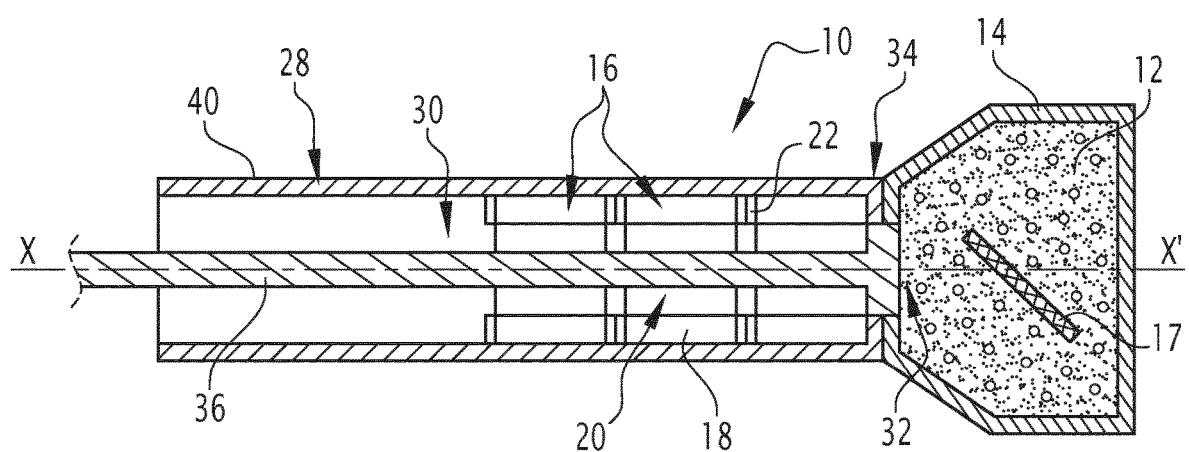
Figure 3:
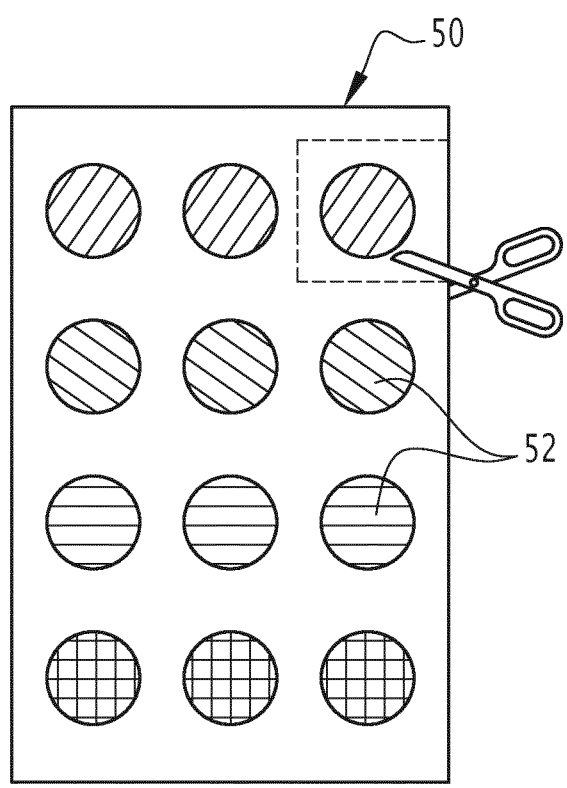
Figure 4:
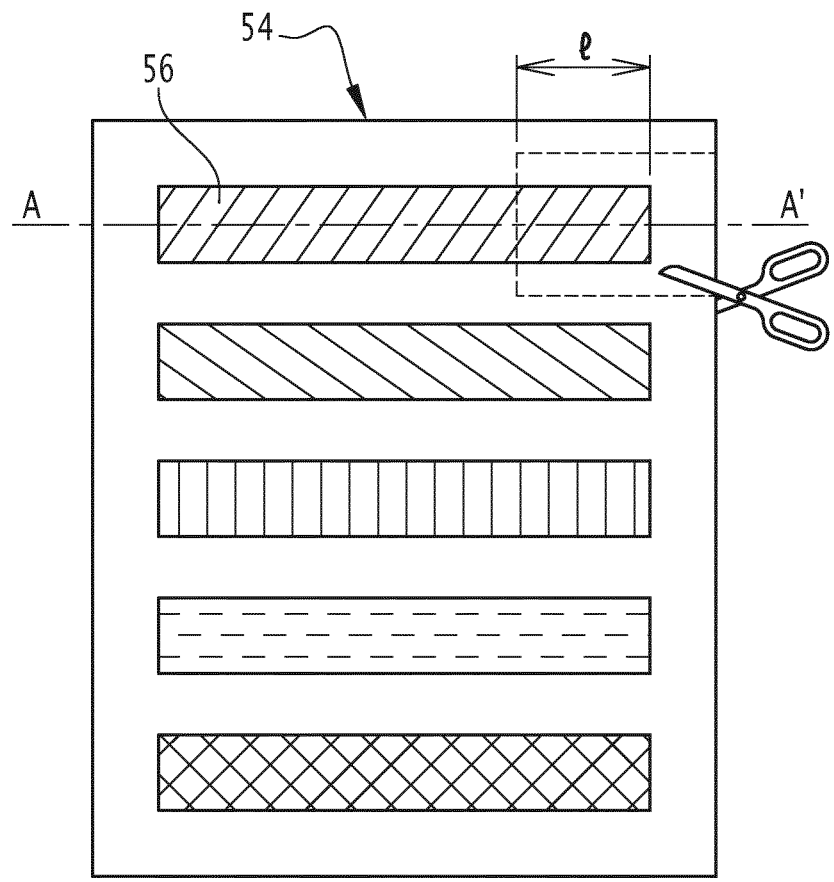
Figure 5:
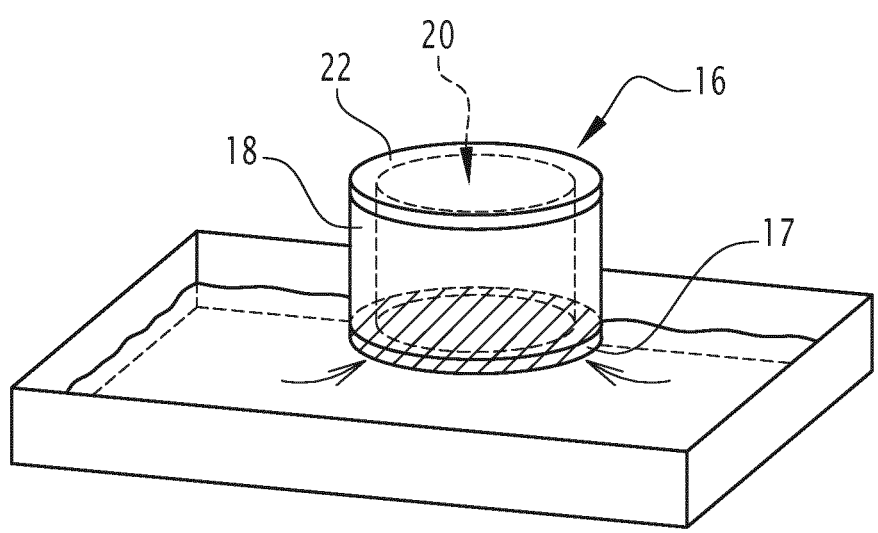

Further features and advantages of the invention will emerge after reading the following description given solely as an example with reference to the appended drawings in which:

FIGS. 1 and 2 show a device for preparing a cosmetic composition according to the invention, during successive steps of a process for preparing, and FIGS. 3 to 5 show different alternatives for preparing the support introduced into the device of FIGS. 1 and 2.

In reference to FIGS. 1 and 2, a device 10 for preparing a cosmetic composition 12 is described.

The device 10 is able to prepare the cosmetic composition 12, by conveying to a receptacle 14 at least one component of the cosmetic composition 12 contained in a capsule 16, and advantageously by conveying and by mixing a plurality of components, contained in at least one capsule 16 or carried by at least one support 17.

The cosmetic composition 12 particularly comprises a cosmetic body surface makeup, care and/or coloring product. The composition 12 is prepared from a plurality of predetermined components, in predetermined precise proportions.

The components of the cosmetic composition 12 comprise for example one or a plurality of liquids, of varied viscosities, aqueous or organic in nature. The components also comprise for example one or a plurality of solids such as powders, particles and/or fibers. Finally, the components comprise for example gels, emulsions, creams, foams, or others.

The cosmetic composition 12 comprises at least one such component in a large quantity, i.e. the volume of the component entering into the cosmetic composition 12 is sufficient for the component to fill at least one of the capsules 16.

The cosmetic composition comprises in addition a component in a small quantity, i.e. present in the cosmetic composition 12 with a volume or mass proportion less than 3%, preferably less than 1%, with respect to the volume or the total mass of the cosmetic composition 12. This quantity of cosmetic product is insufficient to fill a capsule 16 which can be manipulated effectively with the cosmetic composition.

The component is a small quantity comprises for example a perfume, a colorant, a pigment, a preservative, and/or a pH adjuster.

The component in small quantity is typically a customization agent of the cosmetic composition 12.

Each capsule 16 comprises a side wall 18, for example substantially cylindrical, defining a substantially cylindrical inner conduit 20 substantially cylindrical and two seals 22 closing the inner conduit 20 at two opposite ends.

The side wall 18 is in the form of a solid cylindrical sleeve having a substantially constant thickness on the periphery thereof, and a variable length from one capsule 16 to another. The side wall 18 is for example made of plastic material, such as for example methyl polymethacrylate. Alternatively, the side wall 18 is made of glass.

The seals 22 have a thin disk shape and have a diameter substantially equal to the outer diameter of the capsules 16. The seals 22 are attached to a transversal surface of the side wall 18, for example by heat-sealing.

The seals 22 are made of a stretchable material fragile enough to tear when the seals 22 are stretched beyond a rupture threshold. The seals 22 are for example made of rubber, particularly based on a butadiene-acrylonitrile copolymer (referred to as nitrile rubber), or based on a latex.

Alternatively, the seals 22 are made of a fragile material, the presence whereof in the cosmetic composition causes no discomfort, such as for example from sugar, gelatin, wax or others.

According to another alternative, at least one of the seals 22 is made at least partially using a material that absorbs liquids, such as for example paper or fabric, or using a polymer material that has satisfactory absorption properties, for example a cellulose gel.

The inner conduit 20 receives a content of the capsule 16, comprising at least one of the components of the cosmetic composition 12.

Each support 17 is in this example substantially planar, i.e. it extends substantially along a median plane, and its extent along the direction orthogonal to the median plane is less than its extent along each direction of the median plane, in particular five times less, advantageously ten times less.

The support 17 is for example made from paper, in particular paper of the blotting paper type, fabric or using a polymer material that has satisfactory absorption properties, for example a cellulose gel.

Each support 17 receives at least one component of the cosmetic composition 12 in an integral manner. By integral, it is understood that the cosmetic component is connected to the support 17 in a way as to not flow therefrom, but that the cosmetic component can diffuse in a liquid in which the support 17 is dipped. The cosmetic component is for example imprinted on the support 17, adsorbed on the support 17 or soaked in the support 17.

According to an alternative, the support 17 is carried out using a material that is able to spontaneously degrade once dipped into the cosmetic composition 12, for example gelatin.

As shown in FIG. 1, the device 10 comprises a structure 28 defining a housing 30 for receiving the capsules 16 and of the support or supports 17, extending along a longitudinal axis X-X'. The device 10 also comprises an outlet nozzle 32 opening at a first end 34 of the housing 30, and a piston 36 mounted at a second end 38 of the housing 30.

The structure 28 comprises for example a substantially cylindrical casing 40 which defines the housing 30, the outlet nozzle 32 being positioned through the casing 40 and the piston 36 being slidably mounted through the casing 40.

A portion of the structure 28 is movable and/or removable so as to enable the positioning of the capsules 16 in the housing 30.

The housing 30 is a substantially cylindrical internal volume, having a diameter substantially equal to the outer diameter d of the capsules 16. The housing is suitable for receiving the capsule or capsules 16 removably, pressing radially on an internal surface of the housing 30, as well as the support or supports 17, advantageously inserted between two adjacent capsules 16.

Alternatively, the support 17 is attached to a seal 22 of one of the capsules 16, for example in a sticky manner.

The outlet nozzle 32 comprises an opening in the structure 28 opening to the outside of the structure 28 on one side and into the housing 30 on the other side, as well as fastening means of the receptacle 14 (not shown).

Advantageously, the receptacle 14 contains no air when it is positioned on the outlet nozzle 32, which avoids any contamination of the cosmetic composition 12. Alternatively, the receptacle initially contains a neutral gas suitable for preserving the cosmetic composition 12.

The fastening means comprise for example a thread extending onto an internal surface of the opening, suitable for engaging with the thread of the receptacle 14.

Alternatively, the fastening means comprise a clip, bayonet, pin, or other, system.

Alternatively, the receptacle 14 is replaced with a preform that is able to be deformed under the effect of the flow of the contents of the capsules 16 through the outlet nozzle 32, in such a way as to form the receptacle 14 in situ.

The piston 36 is mounted on the structure 28, free to move in translation relative to the structure 28 along the longitudinal axis X-X' in the housing 30, toward the first end 34.

The piston 36 is also free to move through the capsules 16, and suitable for successively stretching the seals 22 of each of the capsules 16 to the rupture threshold thereof and conveying the contents of each capsule 16 toward the outlet nozzle 32, as shown in FIG. 2.

The piston 36 is also able to convey at least a portion of each support 17 arranged in the housing 30 in the direction of the first end 34 and of the outlet nozzle 32, in such a way as to convey the support 17 or the portion of the support 17 to the receptacle 14, as shown in FIG. 2, in such a way that the support 17 or the portion of the support 17 is found in the cosmetic composition 12.

The piston 36 comprises a rod extending along the longitudinal axis X-X', as well at least one piston head arranged in the housing 30, suitable for being set in motion by the rod.

According to an embodiment shown in FIG. 3, the support 17 is made by cutting a sheet 50, in particular a sheet of paper, whereon one or several cosmetic products have been deposited, in particular by impression, spreading, adsorption or spraying, in such a way as to form separate regions 52, with each region 52 comprising the same predetermined unit dose of the cosmetic product.

Advantageously, the sheet 50 comprises several rows of regions 52, with the regions 52 comprising cosmetic products that are different from one row to another.

The regions 52 are for example disks, that have an inner diameter less than the inner diameter of the housing 30.

Each support 17 thus has a planar geometry comprised of a single thickness of material, in particular in the shape of a disk.

Each support 17 is able to be arranged in the housing 30, in contact with a capsule 16, and advantageously inserted between two adjacent capsules 16 as shown in FIG. 1.

Each support 17 extends substantially orthogonally to the longitudinal axis X-X', i.e. the median plane of each support 17 is orthogonal to the longitudinal axis X-X'.

Thus, the quantity of cosmetic product introduced into the cosmetic composition 12 is controlled by cutting a number of regions 52 in the sheet 50 corresponding to the total quantity of the cosmetic product desired for the cosmetic composition 12, expressed as a number of unit doses, in order to form as many supports 17 introduced in the housing 30.

According to another embodiment shown in FIG. 4, the support 17 is a tongue, made by cutting a sheet 54, in particular a sheet of paper, whereon one or several cosmetic products have been deposited, in particular by impression, spreading, adsorption or spraying, in such a way as to form at least one elongated region 56 along an elongation direction A-A'.

Each elongated region 56 has in particular a substantially constant width in the direction orthogonal to the direction of elongation A-A', and advantageously has a substantially rectangular shape elongated along the direction of elongation A-A'.

The support 17 is cut in the sheet, over the entire width of the elongated region 56, and over a length/determined according to the total quantity of the cosmetic product desired for the cosmetic composition 12, and by folding it back along the direction of elongation A-A' if necessary.

The support 17 is folded back as many times as necessary to have a transversal extent less than the inner diameter of the housing 30.

The support 17 is able to be arranged in the housing 30, in contact with a capsule 16, and advantageously inserted between two adjacent capsules 16 as shown in FIG. 1.

The support 17 then has several successive thicknesses of material along the longitudinal axis X-X'.

Thus, the quantity of cosmetic product introduced into the cosmetic composition 12 can be controlled by cutting a single support 17 of a length/variable according to the quantity, and advantageously predetermined in the recipe of the cosmetic composition 12.

According to another embodiment shown in FIG. 5, at least one of the seals 22 of at least one of the capsules 16 constitutes the support 17.

In this embodiment, the seal 22 is constituted of material that absorbs liquids, such as for example paper or fabric, and is connected to the side wall 18 of the capsule 16.

For example, the support 17 is made by soaking with the cosmetic product the seal 22, for example by dipping the initially non-soaked seal 22 into a reservoir containing the cosmetic product long enough to saturate the seal 22.

The quantity of cosmetic product carried by the support 17 then depends on the nature of the material comprising the seal 22 and on its thickness.

Thus, the quantity of cosmetic product intended to be introduced into the cosmetic composition 12 is predetermined, by adjusting the characteristics of the seal 22 beforehand, during the manufacture of the capsule 16.

Alternatively, the seal 22 is pre-soaked beforehand at the manufacturing of the capsule 16, in such a way as to carry a predetermined quantity of cosmetic product.

A process for preparing the cosmetic composition 12 using the preparation device 10 will now be described.

During a preliminary step, a set of capsules 16 comprising one or several capsules 16, as well as at least one support 17, each containing constituents of the composition 12, is selected according to the nature of the composition 12 sought.

During a first step, the capsule or capsules 16 are arranged in the housing 30, in contact with one another.

During the first step, the support or supports 17 are prepared, by cutting and/or by soaking as described hereinabove, and introduced into the housing 30 in contact with the capsules 16.

The process then comprises a step of positioning a receptacle 14 or a preform, connected to the outlet nozzle 32. The receptacle 14 or the preform is fluidically connected, tightly, to the outlet nozzle 32, so as to receive the contents of capsules 16 flowing through the outlet nozzle 32 and fastened by fastening means.

The preform or the receptacle 14 is particularly positioned without introducing into the housing air from outside the device 10.

When the receptacle 14 is positioned, it is particularly empty, such as a folded bag, or contains for example a neutral gas.

The process then comprises a step of moving the piston 36 along the longitudinal axis X-X', toward the outlet nozzle 32, through the housing 30 and through the capsules 16.

The step of moving the piston 36 comprises successive substeps of moving the piston 36 through each first capsule 16, stretching the seals 22 of each capsule 16 to the rupture threshold thereof, and conveying the contents of the first capsules 16 toward the first end 34.

The step of moving the piston also comprises a substep of conveying each support 17 in the direction of the first end 34.

The method then comprises a step of extrusion of the content of each capsule 16 as well as at least a portion of each support 17 through the opening of the outlet nozzle 32, in the receptacle 14. The content of each capsule 16 as well as at least one portion of each support is then in the receptacle 14.

Advantageously, during the movement of the piston 36 and the extrusion of the contents of the capsules 16 and each support 17, the piston 36, the side walls 18 of the capsules 16, the outlet nozzle 32 and the receptacle 14 engage to form a circulation channel fluidically isolated from the outside. The side walls 18 of the capsules 16 and the piston head 36 are in tight contact, making it possible to prevent an entry of air from outside the device 10, which could pollute or contaminate the cosmetic composition 12.

The process finally comprises a step of distributing the cosmetic product carried by each support 17 in the content of the receptacle 14, in such a way as to form the cosmetic composition 12, and/or a step of degradation of the support 17 in the cosmetic composition 12.

Advantageously, the process comprises steps of positioning a new receptacle 14 or a new preform, as well as introducing in the housing 30, removably, of at least one new capsule 16 and of at least one new support 17, as described hereinabove.

The device 10 makes it possible to prepare a great variety of cosmetic compositions 12, by accepting multiple combinations of capsules 16 and of supports 17 each containing one or a plurality of constituents of said cosmetic compositions 12.

The introduction of one or several supports 17 such as described hereinabove into the device 10 makes it possible to add to the cosmetic composition 12 one or several compounds in a small quantity, simply and quickly, and with good control of the quantity introduced and good repeatability.

The invention claimed is:

1. A device for preparing a cosmetic combination, the device comprising:
   a structure defining a housing extending along a longitudinal axis (X-X'), the housing receiving at least one capsule, the or at least one of the capsules containing at least one component of a cosmetic composition,
   an outlet nozzle opening at one end of the housing, suitable for being fluidically connected to a receptacle or to a preform intended to form a receptacle, and
   a piston movable in translation relative to the structure along the longitudinal axis (X-X') in the housing, suitable for perforating the or each capsule and conveying contents of each capsule to the outlet nozzle,
   wherein the device comprises at least one planar support bearing in an integral manner a cosmetic product, each planar support being arranged in the housing, at least one portion of each support being arranged to be driven by the piston into the receptacle containing the cosmetic composition.

2. The device according to claim 1, wherein the cosmetic product is imprinted on the support, adsorbed on the support, or soaks the support.

3. The device according to claim 2, wherein the support is made from paper, fabric, gelatin or a polymer material.

4. The device according to claim 2, wherein the support has a longitudinal extension, measured parallel to the longitudinal axis (X-X'), and a transversal extent, measured perpendicularly to the longitudinal axis (X-X'), with the longitudinal extent being less than the transversal extend.

5. The device according to claim 2, wherein the support is arranged in contact with at least one of the capsules.

6. The device according to claim 2, wherein the support forms a seal that is part of one of the capsules, the support being connected to side walls of the capsule.

7. The device according to claim 1, wherein the support is made from paper, fabric, gelatin or a polymer material.

8. The device according to claim 7, wherein the support has a longitudinal extension, measured parallel to the longitudinal axis (X-X'), and a transversal extent, measured perpendicularly to the longitudinal axis (X-X'), with the longitudinal extent being less than the transversal extend.

9. The device according to claim 7, wherein the support is arranged in contact with at least one of the capsules.

10. The device according to claim 1, wherein the support has a longitudinal extension, measured parallel to the longitudinal axis (X-X'), and a transversal extent, measured perpendicularly to the longitudinal axis (X-X'), with the longitudinal extent being less than the transversal extend.

11. The device according to claim 10, wherein the support is arranged in contact with at least one of the capsules.

12. The device according to claim 10, wherein the transversal extent of the support is less than an inner diameter of the housing, measured perpendicularly to the longitudinal axis (X-X').

13. The device according to claim 12, wherein the support is arranged in contact with at least one of the capsules.

14. The device according to claim 1, wherein the support is arranged in contact with at least one of the capsules.

15. The device according to claim 1, wherein the support forms a seal that is part of one of the capsules, the support being connected to side walls of the capsule.

16. The device according to claim 1, wherein the support is formed from a cutout from a sheet that carries at least one region of cosmetic product.

17. The device according to claim 1, wherein the support is a tongue folded at least one time on itself in such a way as to define several successive layers perpendicular to the central axis X-X'.

18. A process for preparing a cosmetic composition, comprising the following steps:
   providing a device according to claim 1;
   positioning the or each capsule in the housing;
   positioning the or each support in the housing;
   positioning a receptacle or a preform intended to form a receptacle, connected to the outlet nozzle;
   moving the piston in the housing along the longitudinal axis (X-X') toward the one end of the housing, perforation of each capsule on either side of the capsule and conveying the contents of each capsule as well as at least one portion of each support toward the end; and extruding the contents of each capsule and of at least one portion of each support into the receptacle or against the preform, through the outlet nozzle, and obtaining the cosmetic composition.

19. The process for preparing according to claim 18, comprising a step of preparing each support by cutting at least one sheet of material carrying the at least one cosmetic product.

20. The process according to claim 19, wherein the sheet carries a plurality of separate regions of cosmetic product, with the cutting isolating a region of the sheet containing a portion of the separate regions of cosmetic product in order to prepare the support.

\* \* \* \* \*